US011986805B2

(12) United States Patent
Gopal et al.

(10) Patent No.: US 11,986,805 B2
(45) Date of Patent: May 21, 2024

(54) METHOD OF REACTIVATING CATALYST

(71) Applicant: SABIC Global Technologies B.V., Bergen op Zoom (NL)

(72) Inventors: Srikant Gopal, Riyadh (SA); Turki Al-Smari, Riyadh (SA); Shahid Azam, Riyadh (SA); Khalid Karim, Riyadh (SA)

(73) Assignee: SABIC Global Technologies B.V., Bergen op Zoom (NL)

( * ) Notice: Subject to any disclaimer, the term of this patent is extended or adjusted under 35 U.S.C. 154(b) by 472 days.

(21) Appl. No.: 17/431,812

(22) PCT Filed: Mar. 26, 2020

(86) PCT No.: PCT/IB2020/052858
§ 371 (c)(1),
(2) Date: Aug. 18, 2021

(87) PCT Pub. No.: WO2020/194228
PCT Pub. Date: Oct. 1, 2020

(65) Prior Publication Data
US 2022/0143584 A1 May 12, 2022

Related U.S. Application Data

(60) Provisional application No. 62/823,930, filed on Mar. 26, 2019.

(51) Int. Cl.
*B01J 23/96* (2006.01)
*B01J 23/28* (2006.01)
(Continued)

(52) U.S. Cl.
CPC ............... *B01J 23/96* (2013.01); *B01J 23/28* (2013.01); *B01J 23/6525* (2013.01); *B01J 38/18* (2013.01); *C07C 51/215* (2013.01); *C07C 53/08* (2013.01)

(58) Field of Classification Search
CPC ........ B01J 23/28; B01J 23/96; B01J 23/6525; B01J 38/18; C07C 51/215; C07C 53/08
See application file for complete search history.

(56) References Cited

U.S. PATENT DOCUMENTS

| 5,403,798 A | 4/1995 | Brendley, Jr. et al. |
| 6,013,597 A | 1/2000 | Karim et al. |

(Continued)

FOREIGN PATENT DOCUMENTS

| CN | 101421038 A | 4/2009 |
| CN | 101622068 A | 1/2010 |

(Continued)

OTHER PUBLICATIONS

CN Office Action dated Sep. 8, 2023, from related CN Patent Application No. 2020 80024009 filed Mar. 26, 2020; with Engl Transl; 10 pages.

(Continued)

*Primary Examiner* — Yate' K Cutliff
(74) *Attorney, Agent, or Firm* — Womble Bond Dickinson (US) LLP

(57) ABSTRACT

Systems and methods for using and regenerating a catalyst for producing acetic acid from ethane are disclosed. Feed stream comprising ethane and an oxidant including oxygen is flowed to a reactor, in which a catalyst comprising MoVNbPd oxide is disposed. The ethane and the oxidant are reacted in presence of the catalyst under reaction conditions sufficient to produce acetic acid. When the catalyst's ability to catalyze the reaction between the ethane and the oxidant is reduced by a predetermined percentage, the flow of the feed stream to the reactor is ceased. A regenerating gas stream is flowed through the reactor to contact the regenerating gas stream with the catalyst under operating conditions (Continued)

to increase the catalyst's ability to catalyze the reaction between the ethane and the oxidant.

16 Claims, 2 Drawing Sheets

(51) Int. Cl.
*B01J 23/652* (2006.01)
*B01J 38/18* (2006.01)
*C07C 51/215* (2006.01)
*C07C 53/08* (2006.01)

(56) References Cited

U.S. PATENT DOCUMENTS

| | | | |
|---|---|---|---|
| 6,030,920 A | 2/2000 | Karim et al. | |
| 6,130,356 A | 10/2000 | Karim et al. | |
| 6,143,921 A * | 11/2000 | Karim | C07C 67/05 |
| | | | 562/549 |
| 6,156,928 A | 12/2000 | Karim et al. | |
| 6,258,992 B1 | 7/2001 | Karim et al. | |
| 6,310,241 B1 | 10/2001 | Karim et al. | |
| 8,202,814 B2 | 6/2012 | Dieterle et al. | |
| 8,383,854 B2 * | 2/2013 | Ryan | C07C 51/215 |
| | | | 562/548 |
| 9,156,764 B2 * | 10/2015 | Han | C07C 5/3332 |
| 10,626,066 B2 * | 4/2020 | Simanzhenkov | B01J 8/20 |
| 2008/0188695 A1 | 8/2008 | Dieterle et al. | |
| 2011/0009667 A1 | 1/2011 | Ryan et al. | |
| 2015/0045582 A1 | 2/2015 | Han et al. | |
| 2017/0210685 A1 | 7/2017 | Simanzhenkov et al. | |
| 2019/0055176 A1 | 2/2019 | Mitkidis et al. | |

FOREIGN PATENT DOCUMENTS

| | | |
|---|---|---|
| CN | 104203401 A | 12/2014 |
| CN | 107108404 A | 8/2017 |
| WO | WO2004024666 A1 | 3/2004 |
| WO | WO2013148006 A1 | 10/2013 |

OTHER PUBLICATIONS

International Seach Report and Written Opinion from PCT/IB2020/052858 dated Jul. 7, 2020, 11 pages.

* cited by examiner

METHOD OF REACTIVATING CATALYST

CROSS REFERENCE TO RELATED APPLICATIONS

This application is a national phase application under 35 U.S.C. § 371 of International Application No. PCT/IB2020/052858 filed Mar. 26, 2020, which claims priority to U.S. Provisional Patent Application No. 62/823,930 filed Mar. 26, 2019. The entire contents of each of the above-referenced disclosures is specifically incorporated by reference herein without disclaimer.

FIELD OF INVENTION

The present invention generally relates to methods of utilizing and regenerating a catalyst for producing acetic acid. More specifically, the present invention relates to methods of using and regenerating a catalyst adapted to catalyze oxidation of ethane to produce acetic acid.

BACKGROUND OF THE INVENTION

Acetic acid is a chemical reagent used in the production of plastic bottles, photographic films, polyvinyl acetate (for wood glues), and synthetic fibers and fabrics. Acetic acid is also commonly used as a cleaning agent, an acidity regulator for food, and a condiment.

There are several methods of producing acetic acid in the chemical industry. One of the methods is oxidation of ethane. In this process, ethane and an oxidant react in the presence of a catalyst at an elevated temperature and pressure to produce acetic acid. However, the catalyst's performance in this process gradually declines over its time, resulting in various issues including increased carbon dioxide and water formation, increased catalyst temperature, and lower acetic acid productivity.

The increased carbon dioxide and water formation can result in increased energy consumption for the carbon dioxide removal unit and water removal unit used for purifying the acetic acid. Gradually increasing the operating temperature of the catalyst can cause the catalyst to reach a temperature, at which the rate of acetic acid production is significantly lower than when fresh catalyst is used. Furthermore, the increased operating temperature can lead to higher safety risks. When this happens, the replacement of the catalyst is required, which increases the production cost of acetic acid.

Overall, while methods of producing acetic acid exist, the need for improvements in this field persists in light of at least the aforementioned drawbacks of the conventional methods.

BRIEF SUMMARY OF THE INVENTION

A solution to at least some of the above-mentioned problems associated with the production process for acetic acid using ethane and an oxidant has been discovered. The solution resides in a method of using and regenerating a catalyst for producing acetic acid. When the catalyst's ability to catalyze the reaction between the ethane and the oxidant is reduced to or below a predetermined value, typically after 3 to 6 months, or up to 24 months of continuous operation, the method involves flowing an oxygen-containing regeneration gas stream through the catalyst at a temperature to increase the catalyst's ability to catalyze the reaction between the ethane and oxidant. The regenerated catalyst is then used to produce more acetic acid for example another 3 to 6 months, after which regeneration of the catalyst is again carried out. It should be noted that the period between regenerations may vary. So while typically the catalyst can be regenerated every 3 to 6 months, some catalysts may need regenerating only once a year. The regeneration of the catalyst in this way can be beneficial for at least prolonging the catalyst life for the process, thereby reducing the production cost of acetic acid. Notably, this method is capable of reactivating the partially deactivated catalyst to above at least 70% of the activity and selectivity of the fresh catalyst, resulting in lower carbon dioxide and water formation during the production of acetic acid compared to conventional methods. Additionally, regenerating the catalyst can prevent the gradual increase of the catalyst operating temperature, resulting in improved catalyst life and improved safety level for the production system. Therefore, the method of the present invention provides a technical solution to at least some of the problems associated with the currently available methods for producing acetic acid from ethane.

Embodiments of the invention include a method of using and regenerating catalyst for production of acetic acid from ethane. The method includes flowing (1) feed gas comprising ethane and (2) an oxidant comprising oxygen to a reactor, in which a catalyst comprising an MoVNbPd oxide is disposed. The method further includes reacting, in the reactor, the ethane with the oxidant in the presence of the catalyst to produce acetic acid. The method further includes when the catalyst's ability to catalyze the reaction between the ethane and the oxidant is reduced by 30% or more, ceasing the flow of the feed gas and the oxidant to the reactor. The method further still includes flowing a regenerating gas stream comprising 2 to 21 mol. % oxygen at a temperature of 200 to 375° C. and gas hourly space velocity (GHSV) of 1000 to 10,000 h$^{-1}$ through the reactor to contact the regenerating gas stream with the catalyst and thereby increase the catalyst's ability to catalyze the reaction between the ethane and the oxidant.

Embodiments of the invention include a method of using and regenerating catalyst for production of acetic acid from ethane. The method includes flowing (1) feed gas comprising ethane and (2) an oxidant comprising oxygen to a reactor, in which a catalyst comprising an MoVNbPd oxide is disposed. The method further includes reacting, in the reactor, the ethane with the oxidant in presence of the catalyst to produce acetic acid. The method further includes when the catalyst's ability to catalyze the reaction between the ethane and the oxidant is reduced by 30% or more, ceasing the flow of the feed gas and the oxidant to the reactor. The method further includes flushing the feed lines leading to the reactor and the reactor with an inert gas. The method further still includes flowing a regenerating gas stream comprising 2 to 21 mol. % oxygen at a temperature of 200 to 375° C. and GHSV of 1000 to 10,000 h$^{-1}$ through the reactor to contact the regenerating gas stream with the catalyst and thereby increase the catalyst's ability to catalyze the reaction between the ethane and the oxidant. The method further includes purifying the acetic acid produced in the reacting step by removing byproducts including carbon dioxide and/or water.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The term "partially deactivated catalyst", or "deactivated catalyst," as that term is used in the specification and/or claims means a catalyst that has catalytic activity below 70% of that of a fresh catalyst of the same catalyst composition.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

Currently, the method of oxidizing ethane for to produce acetic acid suffers several problems including increasing catalyst temperature over time and gradually declining catalyst activity and selectivity. The declining catalyst activity and selectivity can cause increased carbon dioxide and water formation during the reaction process, resulting in increased energy consumption for separating carbon dioxide and water from the product stream. Furthermore, declining catalyst activity also increases the raw material consumption, resulting in lower production efficiency. The increased catalyst temperature can greatly shorten the life of the catalyst, resulting in increased cost associated with replacing the catalyst. The present invention provides a solution to at least some of these problems. The solution is premised on a method of using and regenerating a catalyst for production of acetic acid from ethane that includes flowing a regenerating gas stream through the catalyst to restore the catalyst activity and selectivity to more than 70% of fresh catalyst when the catalyst performance is dropped to a predetermined value during the reaction of ethane and an oxidant. Generally, the catalyst can be regenerated every 3-6 months, or annually. Thereby, both the overall catalyst performance and the catalyst life have been improved, resulting in improved acetic acid production efficiency and reduced production cost compared to conventional methods. These and other non-limiting aspects of the present invention are discussed in further detail in the following sections.

A. System for Using and Regenerating a Catalyst for Producing Acetic Acid

Figure 1:
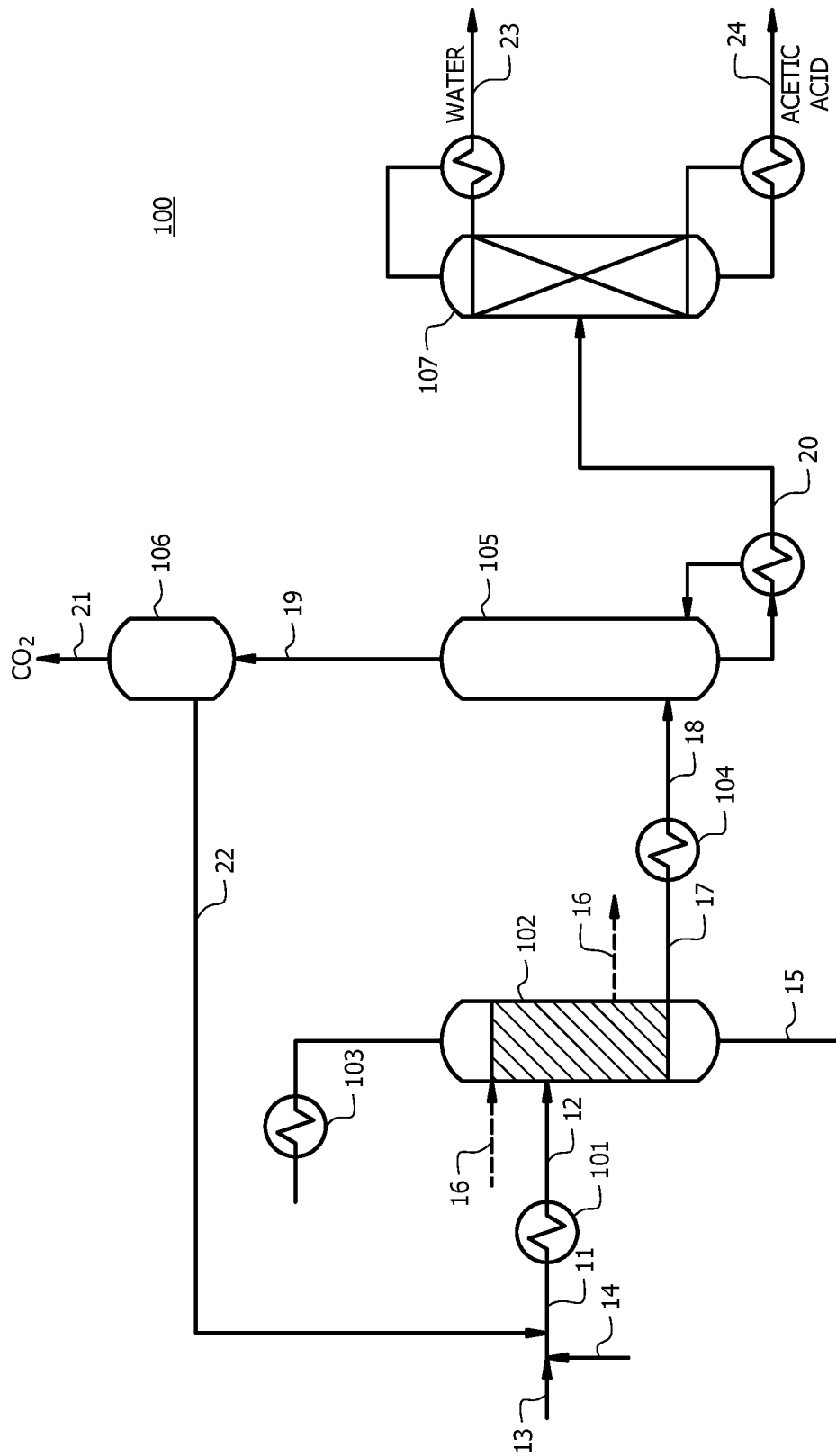
FIG. 1 shows a schematic diagram of a system for using and regenerating a catalyst for producing acetic acid, according to embodiments of the invention.

In embodiments of the invention, the system for using and regenerating a catalyst for producing acetic acid from ethane can include one or more reactors and a product separation system including a carbon dioxide removal unit and a distillation unit. With reference to FIG. 1, a schematic diagram is shown of system 100 that is capable of producing acetic acid from ethane with improved production efficiency and reduced production cost compared to conventional processes. According to embodiments of the invention, system 100 may include feed heating unit 101 adapted to heat feed stream 11 to a predetermined temperature to produce heated feed stream 12. In embodiments of the invention, feed heating unit 101 may comprise a heat exchanger, a furnace, or combinations thereof. The predetermined temperature for feed stream 11 may be in a range of 150 to 450° C. and all ranges and values there between including ranges of 150 to 165° C., 165 to 180° C., 180 to 195° C., 195 to 210° C., 210 to 225° C., 225 to 240° C., 240 to 255° C., 255 to 270° C., 270 to 285° C., 285 to 300° C., 300 to 315° C., 315 to 330° C., 330 to 345° C., 345 to 360° C., 360 to 375° C., 375 to 390° C., 390 to 405° C., 405 to 420° C., 420 to 435° C., and 435 to 450° C. In embodiments of the invention, feed stream 11 may be a combined stream of feed gas stream 13 and oxidant stream 14.

According to embodiments of the invention, an outlet of feed heating unit 101 may be in fluid communication with a first inlet of reaction unit 102 such that heated feed stream 12 flows from feed heating unit 101 to reaction unit 102. In embodiments of the invention, reaction unit 102 may comprise one or more reactors that are adapted to react ethane and the oxidant in the presence of a catalyst under reaction conditions sufficient to produce effluent stream 17 comprising acetic acid. According to embodiments of the invention, effluent stream 17 may further include unreacted ethane, unreacted oxygen, carbon dioxide, water, ethylene, methane, nitrogen, argon, carbon monoxide, low concentrations of various impurities and other by-products, or combinations thereof. In embodiments of the invention, the one or more reactors may be in serial or parallel configuration. Each of the reactors may be a fixed bed reactor of multitubular type, a fluidized bed reactor, or combinations thereof. The reactors may be in comprise multi-tubular configuration. The catalyst disposed in each reactor may include a mixed metal oxide comprising MoVNb, MoVNbTe, MoVNbSb, MoVNbW, MoVNbLa, or combinations thereof. The catalyst may further comprise Pd. The catalyst may be supported on alumina, silica, titania, zinc oxide, or combinations thereof. In embodiments of the invention, the catalyst may have a BET surface area of 10-50 $m^2/g$ for unsupported catalyst and 10-150 $m^2/g$ for supported catalyst, and all ranges and values there between. The catalyst may have a porosity of 0.05 to 0.6 and all ranges and values there between including ranges of 0.05 to 0.06, 0.06 to 0.07, 0.07 to 0.08, 0.08 to 0.09, 0.09 to 0.1, 0.1 to 0.2, 0.2 to 0.3, 0.3 to 0.4, 0.4 to 0.5, and 0.5 to 0.6.

According to embodiments of the invention, each reactor of reaction unit 102 may comprise an inlet and an outlet adapted to receive and release regenerating gas stream 15 therefrom, respectively such that regenerating gas stream 15 flows through the catalyst in each reactor of reaction unit 102. In embodiments of the invention, system 100 may comprise regenerating gas heating unit 103 disposed upstream to the inlet for regenerating gas stream 15. Regenerating gas heating unit 103 may be adapted to heat regenerating gas stream 15 to a predetermined regenerating temperature. In embodiments of the invention, regenerating gas stream 15 may be adapted to restore catalytic activity and selectivity of the catalyst. In embodiments of the invention, regenerating gas stream 15 may be capable of removing hydrocarbon or carbon deposits on the surface of the catalyst, and/or reversing the change in oxidation state of the metal oxide of the catalyst. In embodiments of the invention, regenerating gas stream 15 may comprise 2-21 mol. % oxygen, and 79 to 98 mol. % inert gas. The inert gas may include nitrogen, argon, carbon dioxide, or combinations thereof.

According to embodiments of the invention, each reactor of reaction unit 102 may comprise an inlet and an outlet adapted to receive and release purge gas stream 16 therefrom, respectively such that purge gas stream 16 flows through each reactor. In embodiments of the invention, purge gas stream 16 may be adapted to purge each reactor of reaction unit 102 of hydrocarbon (e.g., ethane). In embodiments of the invention, purge gas stream 16 may include nitrogen, argon, $CO_2$, or combinations thereof. In embodiments of the invention, purge gas stream 16 may be flowed into reaction unit 102 via the same inlet as feed stream 11 such that purge gas stream 16 purges each reactor of reaction unit 102 and the pipelines for flowing feed stream 11 into reaction unit 102.

In embodiments of the invention, an effluent outlet of reaction unit 102 may be in fluid communication with an inlet of effluent cooler 104 such that effluent stream 17 flows from reaction unit 102 to effluent cooler 104. According to embodiments, effluent cooler 104 is adapted to cool effluent stream 17 to produce cooled effluent stream 18. Cooled effluent stream 18 may comprise at least some condensed acetic acid and/or condensed water. In embodiments of the invention, effluent cooler 104 may comprise one or more heat exchangers, one or more quench towers, or combinations thereof.

In embodiments of the invention, the first inlet of reaction unit 102 may be the same as the inlet adapted to receive regenerating gas stream 15, and/or the inlet adapted to receive purge gas stream 16. In embodiments of the invention, the effluent outlet of reaction unit 102 may be the same as the outlet adapted to release regenerating gas stream 15, and/or the outlet adapted to release purge gas stream 16. According to embodiments of the invention, regenerating gas heating unit 103 may be the same as feed heating unit 101.

According to embodiments of the invention, an outlet of effluent cooler 104 may be in fluid communication with gas-liquid separator 105 such that cooled effluent stream 18 flows from effluent cooler 104 to gas-liquid separator 105. In embodiments of the invention, gas-liquid separator 105 may be adapted to separate cooled effluent stream 18 into gaseous stream 19 and liquid stream 20. According to embodiments of the invention, gaseous stream 19 may comprise carbon dioxide, unreacted ethane, unreacted oxidant, or combinations thereof. Liquid stream 20 may comprise water, acetic acid, or combinations thereof. Exemplary gas-liquid separator 105 may include a flash drum, a cold box, a condenser, an acetic acid scrubber, or combinations thereof.

In embodiments of the invention, a top outlet of gas-liquid separator 105 may be in fluid communication with carbon dioxide removal unit 106 such that gaseous stream 19 flows from gas-liquid separator 105 to carbon dioxide removal unit 106. In embodiments of the invention, carbon dioxide removal unit 106 may be adapted to separate gaseous stream 19 into carbon dioxide stream 21 and recycle stream 22. Recycle stream 22 may comprise unreacted ethane, unreacted oxidant, or combinations thereof. In embodiments of the invention, carbon dioxide removal unit 106 may comprise one or more $CO_2$ absorption towers, and one or more regeneration units for $CO_2$ absorption solution. In embodiments of the invention, an outlet of carbon dioxide removal unit 106 may be in fluid communication with an inlet of feed heating unit 101 such that recycle stream combines with feed stream 11 and flows to feed heating unit 101.

According to embodiments of the invention, a bottom outlet of gas-liquid separator 105 may be in fluid communication with an inlet of dewatering unit 107 such that liquid stream 20 flows from gas-liquid separator 105 to dewatering unit 107. In embodiments of the invention, dewatering unit 107 may be adapted to separate liquid stream 20 into water stream 23 and acetic acid stream 24. In embodiments of the invention, dewatering unit 107 may comprise an azeotropic distillation column, a binary distillation column, or combinations thereof. According to embodiments of the invention, the azeotropic distillation column may use ethyl acetate and/or butyl acetate, as an entrainer to form an azeotrope with water.

B. Method of Using and Regenerating a Catalyst for Producing Acetic Acid

Figure 2:
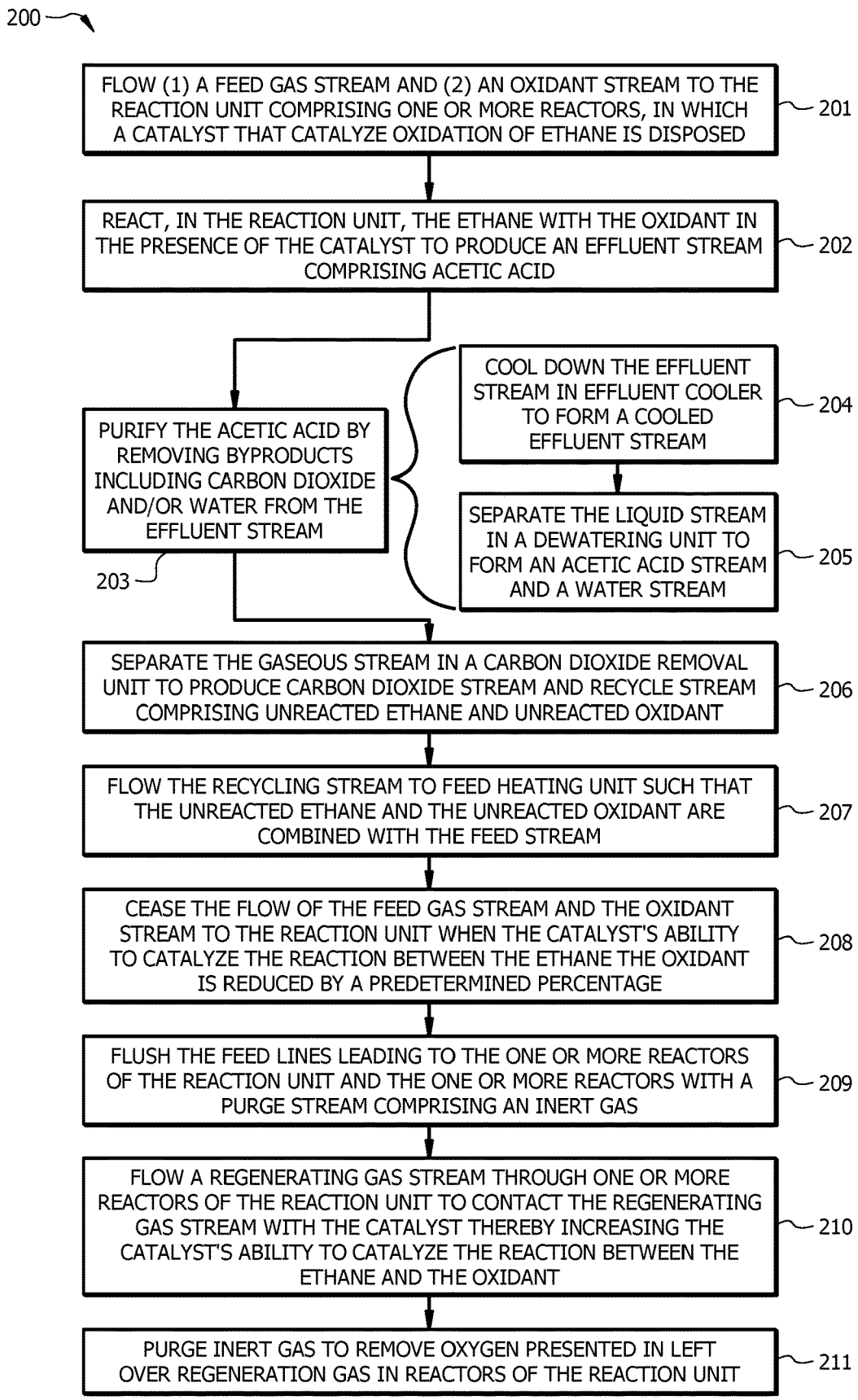
FIG. 2 shows a schematic flowchart of a method of regenerating and using a catalyst for producing acetic acid, according to embodiments of the invention.

Methods of using and regenerating a catalyst for producing acetic acid from ethane have been discovered. The methods may be capable of improving production efficiency and reducing the production cost of acetic acid compared to conventional methods. As shown in FIG. 2, embodiments of the invention include method 200 for using a catalyst for an extended period to produce acetic acid from ethane and then regenerating the catalyst for producing additional acetic acid from ethane over an extended period. Method 200 may be implemented by system 100, as shown in FIG. 1. According to embodiments of the invention, as shown in block 201, method 200 may include flowing (1) feed gas stream 13 and (2) oxidant stream 14 to reaction unit 102 comprising one or more reactors, in which a catalyst that catalyzes oxidation of ethane is disposed, as shown in block 201. In embodiments of the invention, the combined stream (feed stream 11) of feed gas stream 13 and oxidant stream 14 may be heated in feed heating unit 101 before they are flowed to reaction unit 102. In embodiments of the invention, the combined stream (feed stream 11) may be heated to a temperature of 150 to 450° C. and all ranges and values there between including ranges of 150 to 165° C., 165 to 180° C., 180 to 195° C., 195 to 210° C., 210 to 225° C., 225 to 240° C., 240 to 255° C., 255 to 270° C., 270 to 285° C., 285 to 300° C., 300 to 315° C., 315 to 330° C., 330 to 345° C., 345 to 360° C., 360 to 375° C., 375 to 390° C., 390 to 405° C., 405 to 420° C., 420 to 435° C., and 435 to 450° C. In embodiments of the invention, the combined stream (feed stream 11) at block 201 may comprise 0.1 to 50 wt. % oxygen and all ranges and values there between including 0.1 to 0.2 wt. %, 0.2 to 0.3 wt. %, 0.3 to 0.4 wt. %, 0.4 to 0.5 wt. %, 0.5 to 0.6 wt. %, 0.6 to 0.7 wt. %, 0.7 to 0.8 wt. %, 0.8 to 0.9 wt. %, 0.9 to 1.0 wt. %, 1.0 to 5.0 wt. %, 5.0 to 10 wt. %, 10 to 15 wt. %, 15 to 20 wt. %, 20 to 25 wt. %, 25 to 30 wt. %, 30 to 35 wt. %, 35 to 40 wt. %, 40 to 45 wt. %, and 45 to 50 wt. %. In embodiments of the invention, the catalyst may comprise an oxide of Mo, V, Nb, Pd, or combinations thereof. In embodiments of the invention, the catalyst may include a mixed metal oxide comprising MoVNb, MoVNbTe, MoVNbSb, MoVNbW, MoVNbLa, or combinations thereof. The catalyst may further include Pd. According to embodiments of the invention, the catalyst may be supported on alumina, silica, titania, zinc oxide, or combinations thereof.

According to embodiments of the invention, as shown in block 202, method 200 may further comprise reacting, in reaction unit 102, the ethane with the oxidant in the presence of the catalyst to produce effluent stream 17 comprising acetic acid. In embodiments of the invention, effluent stream 17 may further comprise unreacted ethane, unreacted oxidant, carbon dioxide, water, ethylene, methane, nitrogen, argon, or combinations thereof. According to embodiments of the invention, reaction conditions at block 202 may include a reaction temperature in a range of 150 to 450° C. and all ranges and values there between including ranges of 150 to 165° C., 165 to 180° C., 180 to 195° C., 195 to 210° C., 210 to 225° C., 225 to 240° C., 240 to 255° C., 255 to 270° C., 270 to 285° C., 285 to 300° C., 300 to 315° C., 315 to 330° C., 330 to 345° C., 345 to 360° C., 360 to 375° C., 375 to 390° C., 390 to 405° C., 405 to 420° C., 420 to 435° C., and 435 to 450° C. The reaction conditions at block 202 may include a reaction pressure of 1 to 50 bar and all ranges and values there between including ranges of 1 to 5 bar, 5 to 10 bar, 10 to 15 bar, 15 to 20 bar, 20 to 25 bar, 25 to 30 bar, 30 to 35 bar, 35 to 40 bar, 40 to 45 bar, and 45 to 50 bar. The reaction conditions at block 202 may further include a gas hourly space velocity in a range of 50 to 50000 $hr^{-1}$ and all ranges and values there between including ranges of 50 to 100 $hr^{-1}$, 100 to 200 $hr^{-1}$, 200 to 300 $hr^{-1}$, 300 to 400 $hr^{-1}$, 400 to 500 $hr^{-1}$, 500 to 600 $hr^{-1}$, 600 to 700 $hr^{-1}$, 700 to 800 $hr^{-1}$, 800 to 900 $hr^{-1}$, 900 to 1000 $hr^{-1}$, 1000 to 2000 $hr^{-1}$, 2000 to 3000 $hr^{-1}$, 3000 to 4000 $hr^{-1}$, 4000 to 5000 $hr^{-1}$, 5000 to 6000 $hr^{-1}$, 6000 to 7000 $hr^{-1}$, 7000 to 8000 $hr^{-1}$, 8000 to 9000 $hr^{-1}$, 9000 to 10000 $hr^{-1}$, 10000 to 15000 $hr^{-1}$, 15000 to 20000 $hr^{-1}$, 20000 to 25000 $hr^{-1}$, 25000 to 30000 $hr^{-1}$, 30000 to 35000 $hr^{-1}$, 35000 to 40000 $hr^{-1}$, 40000 to 45000 $hr^{-1}$, 45000 to 50000 $hr^{-1}$.

According to embodiments of the invention, method 200 may further comprise purifying the acetic acid by removing byproducts including carbon dioxide and/or water from effluent stream 17, as shown in block 203. In embodiments of the invention, purifying at block 203 may comprise cooling effluent stream 17 in effluent cooler 104 to form cooled effluent stream 18 comprising at least some liquid acetic acid and/or liquid water, as shown in block 204. In embodiments of the invention, purifying at block 203 may further include separating cooled effluent stream 18 in gas-liquid separator 105 into gaseous stream 19 and liquid stream 20.

In embodiments of the invention, liquid-gas separation unit 105 comprises a flash drum. As an alternative to or in addition to a flash drum, liquid-gas separation unit 105 may include an acetic acid scrubber that uses water to scrub uncondensed water from cooled effluent stream 18.

In embodiments of the invention, as shown in block 205, the separating at block 206 may further comprise separating liquid stream 20 in dewatering unit 107 to form acetic acid stream 24, and water stream 23. In embodiments of the invention, dewatering unit 107 comprises one or more azeotropic distillation columns. In embodiments of the invention, an entrainer for the azeotropic distillation column may include ethyl acetate, butyl acetate, or combinations thereof. As an alternative to or in addition to the azeotropic distillation column, dewatering unit 107 may comprise one or more binary distillation columns.

According to embodiments of the invention, as shown in block 206, method 200 may further comprise separating gaseous stream 19 in carbon dioxide removal unit 106 to produce carbon dioxide stream 21 and recycle stream 22 comprising unreacted ethane and unreacted oxidant. In embodiments of the invention, carbon dioxide removal unit 106 may comprise one or more carbon dioxide absorption columns. According to embodiments of the invention, as shown in block 207, method 200 may further comprise flowing recycling stream 22 to feed heating unit 101 such that unreacted ethane and the unreacted oxidant are combined with feed stream 11.

According to embodiments of the invention, as shown in block 208, method 200 further comprises when the catalyst's ability to catalyze the reaction between the ethane and the oxidant is reduced by a pre-determined percentage, ceasing the flow of feed gas stream 13 and oxidant stream 14 to reaction unit 102. In embodiments of the invention, the catalytic activity of the catalyst is reduced by the pre-determined percentage every 3 to 6 months or annually depending on the rate of decline of the catalyst. Hence, in embodiments of the invention, the flow of feed gas stream 13 is ceased every 3 to 6 months or annually to carry out the flushing and regeneration described below. In embodiments of the invention, the catalyst's ability to catalyze the reaction between the ethane and the oxidant may be defined by catalyst activity and/or catalyst selectivity. In embodiments of the invention, the pre-determined percentage of the reduced catalyst ability used at block 203 may be in a range of 20% to 80% and all ranges and values there between including ranges of 20 to 23%, 23 to 26%, 26 to 29%, 29 to 32%, 32 to 35%, 35 to 38%, 38 to 41%, 41 to 44%, 44 to 47%, 47 to 50%, 50 to 53%, 53 to 56%, 56 to 59%, 59 to 62%, 62 to 65%, 65 to 68%, 68 to 71%, 71 to 74%, 74 to 77%, and 77 to 80%. In embodiments of the invention, the fresh catalyst selectivity for producing acetic acid may be in a range of 20 to 80% and all ranges and values there between including ranges of 20 to 25%, 25 to 30%, 30 to 35%, 35 to 40%, 40 to 45%, 45 to 50%, 50 to 55%, 55 to 60%, 60 to 65%, 65 to 70%, 70 to 75%, and 75 to 80%.

In embodiments of the invention, method 200 may further include flushing the feed lines leading to the one or more reactors of reaction unit 102 and the one or more reactors with purge gas stream 16 comprising an inert gas, as shown in block 209. In embodiments of the invention, the inert gas may include nitrogen, argon, carbon dioxide, or combinations thereof.

According to embodiments of the invention, as shown in block 210, method 200 may further comprise flowing regenerating gas stream 15 through one or more reactors of reaction unit 102 to contact regenerating gas stream 15 with the catalyst thereby increasing the catalyst's ability to catalyze the reaction between the ethane and oxidant. In embodiments of the invention, flowing at block 205 may be carried out at a regenerating temperature of 200 to 375° C. and all ranges and values there between including ranges of 200 to 205° C., 205 to 210° C., 210 to 215° C., 215 to 220° C., 220 to 225° C., 225 to 230° C., 230 to 235° C., 235 to 240° C., 240 to 245° C., 245 to 250° C., 250 to 255° C., 255 to 260° C., 260 to 265° C., 265 to 270° C., 270 to 275° C., 275 to 280° C., 280 to 285° C., 285 to 290° C., 290 to 295° C., 295 to 300° C., 300 to 305° C., 305 to 310° C., 310 to 315° C., 315 to 320° C., 320 to 325° C., 325 to 330° C., 330 to 335° C., 335 to 340° C., 340 to 345° C., 345 to 350° C., 350 to 355° C., 355 to 360° C., 360 to 365° C., 365 to 370° C., and 370 to 375° C. The regenerating temperature is selected such that substantially no liquid water was formed in reaction unit 102 during the flowing at block 210. According to embodiments of the invention, the temperature is maintained in reaction unit 102, at least in part, by heating regenerating gas stream 15 via regenerating gas heating unit 103.

In embodiments of the invention, the flowing at block 210 may be carried out such that there is at a gas hourly space velocity in reaction unit 102 in a range of 1000 to 10,000 $hr^{-1}$ and all ranges and values there between including ranges of 1000 to 2000 $hr^{-1}$, 2000 to 3000 $hr^{-1}$, 3000 to 4000 $hr^{-1}$, 4000 to 5000 $hr^{-1}$, 5000 to 6000 $hr^{-1}$, 6000 to 7000 $hr^{-1}$, 7000 to 8000 $hr^{-1}$, 8000 to 9000 $hr^{-1}$, and 9000 to 10,000 $hr^{-1}$. In embodiments of the invention, regenerating gas stream may comprise 2 to 21 mol. % oxygen and all ranges and values there between including ranges of 2 to 3 mol. %, 3 to 4 mol. %, 4 to 5 mol. %, 5 to 6 mol. %, 6 to 7 mol. %, 7 to 8 mol. %, 8 to 9 mol. %, 9 to 10 mol. %, 10 to 11 mol. %, 11 to 12 mol. %, 12 to 13 mol. %, 13 to 14 mol. %, 14 to 15 mol. %, 15 to 16 mol. %, 16 to 17 mol. %, 17 to 18 mol. %, 18 to 19 mol. %, 19 to 20 mol. %, and 20 to 21 mol. %. According to embodiments of the invention, the oxygen fraction in the regenerating gas stream is kept at a low level to substantially prevent oxygen staying in dead pockets of in the catalyst bed. In embodiments of the invention, the flowing at block 210 may be carried out for a duration of 3 to 24 hours. In embodiments of the invention, the flowing at block 210 may be carried out for more than 24 hours. According to embodiments of the invention, the flowing of regenerating gas stream 15 at block 210 may be capable of restoring the activity and/or selectivity of the catalyst to at least 70% of the fresh catalyst (i.e., a catalyst that has not been used in the reacting step at block 202). As an alternative to flowing regenerating gas through reaction unit 102 to regenerate the catalyst, the regenerating of the catalyst may be performed by taking the catalyst out of reaction unit 102 and flowing regenerating gas stream 15 through the catalyst outside of reaction unit 102.

In embodiments of the invention, as shown in block 211, method 200 comprises purging inert gas to remove oxygen presented in left over regeneration gas in reactor(s) of reaction unit 102. Non-limiting examples of purging inert gas may include nitrogen, argon, $CO_2$, and combinations thereof.

According to embodiments of the invention, the one or more reactors in reaction unit 102 may be operated in parallel. Each of the one or more reactors in reaction unit 102 may repeat blocks 201 to 211 every 3 months to every two years, or preferably every 3 months to every 6 months. In embodiments of the invention, reacting at block 202 is carried out in at least one reactor of reaction unit 102 at any moment when system 100 is running.

Although embodiments of the present invention have been described with reference to blocks of FIG. 2, it should be appreciated that operation of the present invention is not limited to the particular blocks and/or the particular order of the blocks illustrated in FIG. 2. Accordingly, embodiments of the invention may provide functionality as described herein using various blocks in a sequence different than that of FIG. 2.

In the context of the present invention, at least the following 15 embodiments are described. Embodiment 1 is a method of using and regenerating catalyst for production of acetic acid from ethane. The method includes flowing (1) feed gas comprising ethane and (2) an oxidant containing oxygen to a reactor, in which a catalyst comprising an MoVNbPd oxide is disposed. The method also includes reacting, in the reactor, the ethane with the oxidant in presence of the catalyst to produce acetic acid. The method further includes, when the catalyst's ability to catalyze the reaction between the ethane and the oxidant is reduced by 30% or more, ceasing the flow of the feed gas and the oxidant to the reactor, and flowing a regenerating gas stream comprising 2 to 21 mol. % oxygen at a temperature of 200 to 375° C. and GHSV of 1000 to 10,000 $h^{-1}$ through the reactor to contact the regenerating gas stream with the catalyst and thereby increase the catalyst's ability to catalyze the reaction between the ethane and the oxidant. Embodiment 2 is the method of embodiment 1, further including, before flowing the regenerating gas stream, flushing feed lines leading to the reactor and the reactor with an inert gas. Embodiment 3 is the method of embodiment 2, wherein the inert gas is selected from the group consisting of nitrogen, argon, $CO_2$, and combinations thereof. Embodiment 4 is the method of any of embodiments 1 to 3, wherein the regenerating gas stream is flowed through the reactor for at least 3 to 24 hours. Embodiment 5 is the method of any of embodiments 1 to 4, wherein the reactor is maintained at a temperature to prevent formation of liquid water. Embodiment 6 is the method of any of embodiments 1 to 5, wherein the regenerating gas stream further contains nitrogen, carbon dioxide, argon, or combinations thereof. Embodiment 7 is the method of any of embodiments 1 to 6, wherein the flowing the regenerating gas through the reactor is capable of restoring the activity of the catalyst to 70 to 100% of a fresh catalyst. Embodiment 8 is the method of any of embodiments 1 to 7, further including recycling unreacted ethane and/or unreacted oxidant to the reactor. Embodiment 9 is the method of any of embodiments 1 to 8, wherein the reactor contains a fixed bed reactor, a fluidized bed reactor, or combinations thereof. Embodiment 10 is the method of any of embodiments 1 to 9, wherein the catalyst is supported on alumina, silica, titania, zinc oxide, or combinations thereof. Embodiment 11 is the method of any of embodiments 1 to 10, wherein the reacting is carried out at a temperature of 150 to 450° C. Embodiment 12 is the method of any of embodiments 1 to 11, wherein the reacting is carried out at a pressure of 1 to 50 bar. Embodiment 13 is the method of any of embodiments 1 to 10, wherein the reacting is carried out at a gas hourly space velocity of 50 to 50000 hr$^{-1}$. Embodiment 14 is the method of any of embodiments 1 to 13, wherein the molar ratio of the oxygen and the ethane flowed into the reactor is in a range of 1:1000 to 1:1. Embodiment 15 is the method of any of embodiments 1 to 14, further including purifying the acetic acid by removing byproducts including $CO_2$ and/or water.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of using and regenerating catalyst for production of acetic acid from ethane, the method comprising:
    flowing (1) feed gas comprising ethane and (2) an oxidant comprising oxygen to a reactor, in which a catalyst comprising an MoVNbPd oxide is disposed;
    reacting, in the reactor, the ethane with the oxidant in presence of the catalyst to produce acetic acid;
    when the catalyst's ability to catalyze the reaction between the ethane and the oxidant is reduced by 30% or more, ceasing the flow of the feed gas and the oxidant to the reactor; and
    flowing a regenerating gas stream comprising 2 to 21 mol. % oxygen at a temperature of 200 to 375° C. and GHSV of 1000 to 10,000 through the reactor to contact the regenerating gas stream with the catalyst and thereby increase the catalyst's ability to catalyze the reaction between the ethane and the oxidant.

2. The method of claim 1, wherein the regenerating gas stream is flowed through the reactor after at least 3 months of operation of the reactor.

3. The method of claim 1, further comprising, before flowing the regenerating gas stream, flushing feed lines leading to the reactor and the reactor with an inert gas.

4. The method of claim 3, wherein the inert gas is selected from the group consisting of nitrogen, argon, $CO_2$, and combinations thereof.

5. The method of claim 1, to wherein the regenerating gas stream is flowed through the reactor for at least 3 to 24 hours.

6. The method of claim 1, wherein the reactor is maintained at a temperature to prevent formation of liquid water.

7. The method of claim 1, wherein the regenerating gas stream further comprises nitrogen, carbon dioxide, argon, or combinations thereof.

8. The method of claim 1, wherein the flowing the regenerating gas through the reactor is capable of restoring the activity of the catalyst to 70 to 100% of a fresh catalyst.

9. The method of claim 1, further comprising recycling unreacted ethane and/or unreacted oxidant to the reactor.

10. The method of claim 1, wherein the reactor comprises a fixed bed reactor, a fluidized bed reactor, or combinations thereof.

11. The method of claim 1, wherein the catalyst is supported on alumina, silica, titania, zinc oxide, or combinations thereof.

12. The method of claim 1, wherein the reacting is carried out at a temperature of 150 to 450° C.

13. The method of claim 1, wherein the reacting is carried out at a pressure of 1 to 50 bar.

14. The method of claim 1, wherein the reacting is carried out at a gas hourly space velocity of 50 to 50000 hr$^{-1}$.

15. The method of claim 1, wherein the molar ratio of the oxygen and the ethane flowed into the reactor is in a range of 1:1000 to 1:1.

16. The method of claim 1, further comprising purifying the acetic acid by removing byproducts including $CO_2$ and/or water.

* * * * *

UNITED STATES PATENT AND TRADEMARK OFFICE
CERTIFICATE OF CORRECTION

PATENT NO. : 11,986,805 B2
APPLICATION NO. : 17/431812
DATED : May 21, 2024
INVENTOR(S) : Srikant Gopal et al.

Page 1 of 1

It is certified that error appears in the above-identified patent and that said Letters Patent is hereby corrected as shown below:

In the Claims

On Column 11, Line 44, after "10,000" please insert --$h^{-1}$--.

On Column 12, Line 13, after "claim 1," please delete "to".

Signed and Sealed this
Twenty-fifth Day of February, 2025

Coke Morgan Stewart
*Acting Director of the United States Patent and Trademark Office*